(12) United States Patent
Isobe et al.

(10) Patent No.: US 10,072,275 B2
(45) Date of Patent: Sep. 11, 2018

(54) METHOD OF PRODUCING 2,3-BUTANEDIOL

(71) Applicant: Toray Industries, Inc., Tokyo (JP)

(72) Inventors: Kyohei Isobe, Kamakura (JP); Kenji Sawai, Kamakura (JP); Kenji Kawamura, Kamakura (JP); Katsushige Yamada, Kamakura (JP); Hideshi Yanase, Tottori (JP)

(73) Assignee: Toray Industries, Inc. (JP)

(*) Notice: Subject to any disclaimer, the term of this patent is extended or adjusted under 35 U.S.C. 154(b) by 127 days.

(21) Appl. No.: 15/037,735

(22) PCT Filed: Nov. 19, 2014

(86) PCT No.: PCT/JP2014/080571
§ 371 (c)(1),
(2) Date: May 19, 2016

(87) PCT Pub. No.: WO2015/076279
PCT Pub. Date: May 28, 2015

(65) Prior Publication Data
US 2016/0298144 A1 Oct. 13, 2016

(30) Foreign Application Priority Data

Nov. 22, 2013 (JP) ................. 2013-241869
Oct. 22, 2014 (JP) ................. 2014-215075

(51) Int. Cl.
*C12P 7/02* (2006.01)
*C12P 7/18* (2006.01)
*C12N 1/20* (2006.01)
*C12N 15/52* (2006.01)

(52) U.S. Cl.
CPC ............ *C12P 7/18* (2013.01); *C12N 1/20* (2013.01); *C12N 15/52* (2013.01)

(58) Field of Classification Search
CPC ............ C12P 7/02; C12P 7/16; C12P 7/18
See application file for complete search history.

(56) References Cited

U.S. PATENT DOCUMENTS

2007/0298476 A1    12/2007  Yanase et al.
2016/0177346 A1*   6/2016   Kawakami ............... C12N 1/14
                                                           435/128

FOREIGN PATENT DOCUMENTS

| JP | 2005-261421 A | 9/2005 |
| JP | 2011-522563 A | 8/2011 |
| WO | 95/28476 | 10/1995 |
| WO | 2008/000809 A1 | 1/2008 |
| WO | 2013/054874 A1 | 4/2013 |

OTHER PUBLICATIONS

Bourns, A.N., et al., "The Catalytic Action of Aluminum Silicates: 1. The Dehydration of Butanediol-2, 3 and Butanone-2 Over Activated Morden Bentonite," *Canadian Journal of Research*, 25(b)1, pp. 80-89, 1947, Abstract only.

Shlechter, N., et al. "Pyrolysis of 2,3-Butylene Glycol Diacetate to Butadiene," *Industrial and Engineering Chemistry*, vol. 37, No. 9, Sep. 1945, pp. 905-908.

Singaporean Written Opinion dated Feb. 17, 2017, of corresponding Singaporean Application No. 11201604094V.

Norman B. Jansen et al., "Production of 2,3-butanediol from D-xylose by *Klebsiella oxytoca* ATCC 9724," Biotechnology and Bioengineering, vol. 26, Issue 4, Apr. 1984, pp. 362-369 (Abstract).

Tomoyuki Okamoto et al., "*Zymobacter palmae* gen. nov., sp. nov., A new ethanol-fermenting peritrichous bacterium isolated from palm sap," Archives of Microbiology, vol. 160, Issue 5, Nov. 1993, pp. 333-337 (Abstract).

B. Herold et al., "Determination of the Three Isomers of 2,3-Butanediol Formed by Yeasts or Lactic Acid Bacteria During Fermentation," American Journal of Enology and Viticulture, vol. 46, No. 1, Jan. 1995, pp. 134-137 (Abstract).

Smita S. Nilegaonkar et al., "Potential of *Bacillus licheniformis* for the production of 2,3-butanediol," Journal of Fermentation and Bioengineering, vol. 82, Issue 4, 1996, pp. 408-410 (Abstract).

B. Marwoto et al., "Metabolic analysis of acetate accumulation during xylose consumption by *Paenibacillus polymyxa*," Applied Microbiology and Biotechnology, vol. 64, Issue 1, Mar. 2004, pp. 112-119 (Abstract).

Cuiqing Ma et al., "Enhanced 2,3-butanediol production by *Klebsiella pneumoniae* SDM," Applied Microbiology and Biotechnology, vol. 82, Issue 1, Feb. 2009, pp. 49-57 (Abstract).

Xiao-Jun Ji et al., "Engineering *Klebsiella oxytoca* for efficient 2,3-butanediol production through insertional inactivation of acetaldehyde dehydrogenase gene," Applied Microbiology and Biotechnology, vol. 85, Issue 6, Feb. 2010, pp. 1751-1758 (Abstract).

Zheng-Jun Li et al., "Microbial production of meso-2,3-butanediol by metabolically engineered *Escherichia coil* under low oxygen condition," Applied Microbiology and Biotechnology, vol. 87, Issue 6, Aug. 2010, pp. 2001-2009 (Abstract).

Marco A.J. Siemerink et al., "D-2,3-Butanediol Production Due to Heterologous Expression of an Acetoin Reductase in *Clostridium acetobutylicum*," Applied and Environmental Microbiology, vol. 77, No. 8, Apr. 2011, pp. 2582-2588.

Taowei Yang et al., "Optimization and scale-up of 2,3-butanediol production by *Bacillus amyloliquefaciens* B10-127," World Journal of Microbiology and Biotechnology, vol. 28, Issue 4, Apr. 2012, pp. 1563-1574 (Abstract).

(Continued)

*Primary Examiner* — Maryam Monshipouri
(74) *Attorney, Agent, or Firm* — DLA Piper LLP (US)

(57) ABSTRACT

A method of producing 2,3-butanediol includes the steps of: culturing a microorganism belonging to the genus *Zymobacter* in a fermentation feedstock containing a carbon source (Step A); and purifying 2,3-butanediol from culture liquid obtained in this step (Step B). In this method, the carbon source contains pentose, and the microorganism belonging to the genus *Zymobacter* has a capacity to metabolize pentose.

14 Claims, No Drawings

(56) References Cited

OTHER PUBLICATIONS

Qingzhao Wang et al., "Metabolic engineering of thermophilic *Bacillus licheniformis* for chiral pure D-2,3-butanediol production," Biotechnology and Bioengineering, vol. 109, Issue 7, Jul. 2012, pp. 1610-1621 (Abstract).

Soo-Jung Kim et al., "Production of 2,3-butanediol by engineered *Saccharomyces cerevisiae*," Bioresource Technology, vol. 146, Jul. 2013, pp. 274-281 (Abstract).

Supplementary European Search Report dated Jun. 21, 2017, of corresponding European Application No. 14864767.0.

\* cited by examiner

METHOD OF PRODUCING 2,3-BUTANEDIOL

TECHNICAL FIELD

This disclosure relates to a method of producing 2,3-butanediol by microbial fermentation.

BACKGROUND 2,3-Butanediol (which may hereinafter be referred to as "2,3-BDO") is a useful compound used as an intermediate material for pharmaceuticals and cosmetics, and as a material for inks, perfumes, liquid crystals, insecticides, softening agents, explosives, plasticizers, and the like. More specifically, for example, 2,3-butanediol can be used as a material for methyl ethyl ketone (A. N. Bourns, The Catalytic Action of Aluminium Silicates, Canadian J. Res. (1947)) or 1,3-butadiene (Nathan Shlechter, Pyrolysis of 2,3-butylene Glycol Diacetate to Butadiene, Indu. Eng. Chem. 905 (1945)). Industrially, 2,3-BDO is produced by a method in which 2-butene oxide is hydrolyzed in an aqueous perchloric acid solution. In recent years, to solve the problems of depletion of petroleum resources and global warming, achievement of a sustainable, recycling-oriented society is demanded. Also, in the chemical industry, shifting from petroleum materials to biomass-derived materials is being intensively studied. Under such circumstances, methods of producing 2,3-butanediol by microbial fermentation have begun attracting attention.

Known examples of microorganisms capable of efficiently producing 2,3-butanediol by fermentation include enterobacteria such as *Klebsiella pneumoniae* (Ma C Q, Enhanced 2,3-butanediol production by *Klebsiella pneumoniae* SDM, Appl Microbiol Biotechnol 2009; 82:49-57) and *Klebsiella oxytoca* (Ji X J, Engineering *Klebsiella oxytoca* for efficient 2,3-butanediol production through insertional inactivation of acetaldehyde dehydrogenase gene, Appl Microbiol Biotechnol 2010; 85:1751-8). Since these microorganisms do not require a particular vitamin, amino acid, or the like for the fermentation, their use is advantageous in that the processes required for isolation/purification of 2,3-butanediol from the fermentation liquid can be reduced. However, these microorganisms are pathogenic, and known to cause respiratory infections and the like. Therefore, when large-scale culture of these fermentation microorganisms is carried out for the purpose of industrial production of 2,3-butanediol, facilities for strict control are required, and the cost increases as a result.

There are disclosed methods using biologically safe 2,3-butanediol fermentation microorganisms showing high fermentation efficiency such as bacteria belonging to the family Bacillaceae including *Bacillus licheniformis* (S. S. Nilegaonkar, Potential of *Bacillus licheniformis* for the production of 2,3-butanediol, Journal of Fermentation and Bioengineering, Vol. 82, Issue 4, 1996, pages 408-410) and *Bacillus amyloliquefaciens* (Yang T, Optimization and scale-up of 2,3-butanediol production by *Bacillus amyloliquefaciens* B10-127, World J Microbiol Biotechnol, 2012 April; 28(4): 1563-74). However, 2,3-butanediol fermentation by *Bacillus licheniformis* requires use of an animal extract, which is expensive, as a nutrient source for promoting the fermentation. 2,3-Butanediol fermentation by *Bacillus amyloliquefaciens* requires use of ammonium citrate for promotion of the fermentation. Since the boiling point of citric acid is close to that of 2,3-butanediol, isolation/purification of 2,3-butanediol is difficult when citric acid remains in the culture liquid.

On the other hand, as fermentation feedstocks for microbial fermentation, not only conventional sugars derived from edible biomass, but also sugars derived from non-edible biomass are attracting attention. When a sugar derived from non-edible biomass is used as the fermentation feedstock, cellulose, hemicellulose and the like contained in the non-edible biomass are decomposed into sugars using a saccharifying enzyme. In that process, pentoses such as xylose are obtained in addition to hexoses such as glucose. Therefore, development of an efficient fermentation technique for materials containing pentose has been demanded.

Known examples of microorganisms capable of efficiently producing 2,3-butanediol from pentose by fermentation include enterobacteria such as *Klebsiella oxytoca* (Ma C Q, Enhanced 2,3-butanediol . . . ). Since these microorganisms do not require a particular vitamin, amino acid or the like for the fermentation, their use is advantageous in that the processes required for purification of 2,3-butanediol from the fermentation liquid can be reduced. However, these microorganisms are pathogenic, and known to cause respiratory infections and the like. Therefore, when large-scale culture of these fermentation microorganisms is carried out for the purpose of industrial production of 2,3-butanediol, facilities for strict control are required, and the cost increases as a result.

On the other hand, there are disclosed methods using biologically safe microorganisms capable of producing 2,3-butanediol from pentose by fermentation such as bacteria belonging to the family Bacillaceae including *Bacillus licheniformis* (Wang Q, Metabolic engineering of thermophilic *Bacillus licheniformis* for chiral pure D-2,3-butanediol production, Biotechnol Bioeng, 2012 July: 109(7): 1610-21) and *Paenibacillus polymyxa* (Marwoto B, Metabolic analysis of acetate accumulation during xylose consumption by *Paenibacillus polymyxa*, Appl Microbiol Biotechnol, 2004 March: 64(1):112-9). However, in 2,3-butanediol fermentation using these microorganisms, an expensive auxiliary material such as a yeast extract or animal protein hydrolysate needs to be used so that the cost is high.

There are known transformed microorganisms belonging to the genus *Zymobacter* and having a capacity to metabolize pentose, which microorganisms were prepared by introducing exogenous genes encoding xylose isomerase, xylulokinase, transaldolase, and transketolase into microorganisms belonging to the genus *Zymobacter* (JP 2005-261421 A, US 2007/0298476 A). However, although JP '421 and US '476 describe that the transformed microorganisms have a capacity to produce ethanol, there is neither description nor suggestion on a capacity to produce 2,3-butanediol from pentose by fermentation.

As described above, when a biologically safe microorganism is used in a conventional method of producing 2,3-butanediol by microbial fermentation, the cost is high, or separation from a by-product is difficult, which is problematic.

Accordingly, it could be helpful to provide a method of producing 2,3-butanediol by microbial fermentation utilizing a biologically safe microorganism and an economical method of producing 2,3-butanediol from a fermentation feedstock containing pentose as a carbon source, by microbial fermentation utilizing a biologically safe microorganism.

SUMMARY

We discovered that bacteria belonging to the genus *Zymobacter*, which have not been known as 2,3-butanediol fermentation microorganisms, have a capacity of 2,3-butanediol fermentation. In addition, we discovered that 2,3-butanediol can be produced from pentose by using a *Zymobacter* bacterium having a capacity to metabolize pentose.

We thus provide as described in (1) to (16) below.

(1) A method of producing 2,3-butanediol, comprising the steps of:
culturing a microorganism belonging to the genus *Zymobacter* in a fermentation feedstock containing a carbon source (Step A); and
purifying 2,3-butanediol from culture liquid obtained in the above step (Step B).

(2) The method according to (1), wherein the microorganism is *Zymobacter* palmae.

(3) The method according to (1) or (2), wherein the Step A is culturing under aerated conditions.

(4) The method according to any one of (1) to (3) wherein the Step A is culturing at a volumetric oxygen transfer coefficient (kLa) of not less than 9 $h^{-1}$.

(5) The method according to any one of (1) to (4), wherein the Step A is culturing at a pH of 5 to 7.

(6) The method according to any one of (1) to (5), wherein the Step A is culturing in a medium whose total sugar concentration is not less than 20 g/L.

(7) The method according to any one of (1) to (6), wherein the carbon source contains pentose, and the microorganism belonging to the genus *Zymobacter* has a capacity to metabolize pentose.

(8) The method according to any one of (1) to (7), wherein the microorganism is a transformed microorganism belonging to the genus *Zymobacter* in which an exogenous gene(s) encoding at least one enzyme selected from the group consisting of xylose isomerase, xylulokinase, transaldolase, and transketolase is/are introduced.

(9) The method according to (8), wherein the microorganism is a transformed microorganism belonging to the genus *Zymobacter* in which exogenous genes encoding xylose isomerase, xylulokinase, transaldolase, and transketolase are introduced.

(10) The method according to any one of (7) to (9), wherein the pentose contained in the fermentation feedstock in the Step A is xylose.

(11) The method according to any one of (7) to (10), wherein the abundance of xylose with respect to total sugar in the fermentation feedstock is 5 to 100%.

(12) The method according to any one of (7) to (11), wherein the fermentation feedstock contains a sugar liquid derived from a biomass.

(13) The method according to any one of (1) to (12), wherein the fermentation feedstock in the Step A contains corn steep liquor.

(14) The method according to any one of (1) to (13), wherein the Step B comprises a distillation process.

(15) The method according to (14), comprising a desalting process before the distillation process.

(16) The method according to (15), comprising an ion-exchange process as the desalting process.

In a method of producing 2,3-butanediol from a fermentation feedstock by microbial fermentation, 2,3-butanediol can be more safely and economically obtained compared to conventional techniques. Even when the fermentation feedstock contains pentose as a carbon source, 2,3-butanediol can be safely and economically obtained from the pentose.

DETAILED DESCRIPTION

Step A: 2,3-Butanediol Fermentation Step

Our method is characterized in that a bacterium belonging to the genus *Zymobacter* is used as a 2,3-butanediol (which may hereinafter be referred to as "2,3-BDO") fermentation microorganism. The microorganism used may be a microorganism isolated from the natural environment, or may be a microorganism whose properties are partially modified by mutation or genetic recombination. Specific examples of the bacteria belonging to the genus *Zymobacter* having a 2,3-BDO fermentation capacity include *Zymobacter palmae*, which is preferably used from the viewpoint of the 2,3-BDO fermentation capacity.

The fermentation feedstock is preferably an ordinary liquid medium containing, as appropriate, one or more of metabolizable carbon sources, metabolizable nitrogen sources, inorganic salts and, if necessary, amino acids and organic micronutrients such as vitamins. The fermentation feedstock may also contain an antifoaming agent as appropriate for the purpose of efficient fermentation.

Specific examples of the metabolizable carbon sources include sugars such as glucose, mannose, galactose, fructose, sucrose, starch, waste molasses, and starch; organic acids such as citric acid, succinic acid, and acetic acid; and alcohols such as glycerol and ethanol. Sugars are preferred. When a sugar is used, the concentration of the sugar in the medium is usually not less than 15 g/L, preferably not less than 20 g/L from the viewpoint of efficiently carrying out the later step of purifying 2,3-butanediol. The total sugar concentration in the fermentation feedstock as the medium is usually 15 to 500 g/L, preferably 20 to 300 g/L. When the total sugar concentration is not more than 15 g/L, the effect of increasing the yield from the carbon source may decrease. When the total sugar concentration is low, production efficiency of 2,3-BDO also decreases.

Specific examples of the metabolizable nitrogen sources include ammonia gas, aqueous ammonia, ammonium salts, urea, nitrates, and amino acids; and organic nitrogen sources which can be supplementarily used such as oil cakes, soybean hydrolysates, casein hydrolysates, animal tissue hydrolysates, corn steep liquor, yeasts or yeast extracts, meat extracts, and fermentation microorganism cells and hydrolysates thereof. Among these, as the organic nitrogen sources, soybean hydrolysates and corn steep liquor are preferred. Corn steep liquor is more preferred. The concentration of the corn steep liquor contained in the fermentation feedstock is not limited. For example, the concentration is usually 2.5 g/L to 35 g/L, preferably 5 g/L to 25 g/L, more preferably 10 g/L to 20 g/L in terms of the solid content contained in the corn steep liquor. The method of measuring the solid content contained in the corn steep liquor is not limited. The solid content can be calculated by, for example, determining the water content based on the difference between the weight before heat drying and the weight after heat drying, and subtracting the water content from the weight before drying. Examples of inorganic salts which may be added as appropriate include phosphoric acid salts, magnesium salts, calcium salts, iron salts, and manganese salts.

In addition, nicotinic acid may be added to the medium as appropriate depending on the growth of the microorganism. An antifoaming agent may also be added as appropriate.

The culture temperature is not limited as long as it is a temperature within the range allowing growth of the microorganism. The culturing is carried out at a temperature of usually 20 to 50° C., preferably 25 to 40° C. The culture period may be a period during which 2,3-BDO accumulates, in the medium, in an amount allowing purification of the 2,3-BDO. The culture period can be appropriately set by monitoring the concentration of the carbon source or the concentration of 2,3-BDO produced in the medium with time. The culture period is not limited, and usually 1 hour to 300 hours, preferably 4 hours to 150 hours.

The pH of the medium during the culturing is maintained within the range of, usually, 4 to 8 by using an inorganic or organic acid, alkaline substance, urea, calcium carbonate, ammonia gas and/or the like. The pH during the culturing is preferably adjusted to 5 to 7. The pH is more preferably not less than 5 and less than 6.

The mode of the culturing of the microorganism is not limited. The culturing is carried out by, for example, batch culture, fed-batch fermentation, or continuous culture.

The microorganism is preferably cultured under aerated conditions. Aeration means that a gas containing oxygen is allowed to flow into a culture vessel. Examples of the method of aeration include, but are not limited to, a method in which a gas containing oxygen is passed through the culture medium, and upper surface aeration in which the air layer on the culture liquid is replaced with a gas containing oxygen. Examples of the upper surface aeration include a method in which a gas containing oxygen is blown into the culture vessel, and a method in which an air flow is generated on the culture liquid by stirring the culture liquid in a state where the culture liquid is exposed to the atmosphere, thereby supplying oxygen into the culture liquid. Aeration is preferably carried out by a method in which a gas containing oxygen is passed through the culture liquid.

In culturing a microorganism, conditions of supplying oxygen into the medium can be appropriately set by combination of aeration and stirring. The conditions are expressed by the volumetric oxygen transfer coefficient, kLa ($h^{-1}$) (hereinafter simply referred to as kLa) for water at normal pressure at 30° C. kLa represents a capacity to produce dissolved oxygen by transferring oxygen from a gas phase to a liquid phase in a unit time under aeration and stirring, and is defined according to Equation (1) (Laboratory Manual for Bioengineering. The Society for Biotechnology, Japan ed., Baifukan Co., Ltd., p. 310 (1992)).

$$dC/dt = kLa \times (C^* - C) \quad (1)$$

In this equation, C represents the dissolved oxygen level DO (ppm) in the culture liquid; $C^*$ represents the dissolved oxygen level DO (ppm) in the equilibrium state with the gas phase in the absence of oxygen consumption by the microorganism; and kLa represents the volumetric oxygen transfer coefficient ($hr^{-1}$). Since Equation (2) is derived from Equation (1), kLa can be determined by plotting the logarithm of $C^*-C$ against the aeration period.

$$\ln(C^* - C) = -kLa \times t \quad (2)$$

The kLa is a value measured by the gas replacement method (dynamic method). In the gas replacement method (dynamic method), water is fed to an aeration/agitation culture apparatus into which a dissolved-oxygen level electrode is inserted, and oxygen in the liquid is replaced with nitrogen to reduce the oxygen concentration in the liquid. Subsequently, the nitrogen gas is switched to compressed air, and the process of increase in the dissolved oxygen is measured at a predetermined aeration rate, stirring rate, and temperature, thereby calculating kLa.

The kLa set for the culturing is not limited, and preferably not less than 9 $h^{-1}$. The upper limit of the kLa is not limited, and the kLa is preferably not more than 200 $h^{-1}$.

The fermentation feedstock contains pentose as a metabolizable carbon source in the method. By culturing a microorganism belonging to the genus *Zymobacter* having a capacity to metabolize pentose, 2,3-butanediol can be produced using the pentose as a material. In such a case, the bacterium belonging to the genus *Zymobacter* may be a bacterium isolated from the natural environment, or may be a bacterium whose properties were partially modified by mutation or genetic recombination. Specific examples of the bacterium belonging to the genus *Zymobacter* having a capacity of 2,3-butanediol fermentation include *Zymobacter palmae*, which is preferably used from the viewpoint of the 2,3-butanediol fermentation capacity. Normally, *Zymobacter palmae* does not metabolize pentose. However, the capacity to metabolize pentose can be given thereto by introduction of a gene(s) involved in pentose metabolism.

A gene for an enzyme which isomerizes aldopentose to ketopentose may be used. Examples of the gene include genes for pentose isomerase, pentose reductase, and/or pentol dehydrogenase.

Pentose isomerase is defined as an enzyme that catalyzes isomerization of aldopentose and ketopentose, which are structural isomers of pentose. The pentose isomerase is not limited as long as it has activity to catalyze direct isomerization of pentose. Examples of the pentose isomerase include xylose isomerase (EC 5.3.1.5) and arabinose isomerase (EC 5.3.1.3). Among these, xylose isomerase is an enzyme that catalyzes direct isomerization of xylose (aldopentose) to xylulose (ketopentose), and/or the reverse reaction thereof, and also known as xylose ketoisomerase. The direct isomerization means one-step isomerization catalyzed by pentose isomerase, which is different from two-step conversion through a sugar alcohol intermediate catalyzed by pentose reductase and pentol dehydrogenase.

Pentose reductase is a reducing enzyme, and means an enzyme having an activity to convert an aldopentose into a sugar alcohol using NADH or NADPH as a coenzyme. For example, EC 1.1.1.307 and EC 1.1.1.21 correspond to xylose reductase, which is an enzyme that converts xylose to xylitol. For example, EC 1.1.1.21 corresponds to arabinose reductase, which is an enzyme that converts arabinose to arabitol. Enzymes that are not categorized into the EC numbers described above are also included in the pentose reductase as long as the enzymes have the activities described above.

Pentol dehydrogenase is a dehydrogenase, and means an enzyme that converts pentol to ketopentose using NAD+ as a coenzyme. For example, EC 1.1.1.9 and EC 1.1.1.10 correspond to xylitol dehydrogenase, which is an enzyme that converts xylitol to xylulose. For example, EC 1.1.1.11 and EC 1.1.1.12 correspond to arabitol dehydrogenase, which is an enzyme that converts arabitol to ribose. Enzymes not categorized into pentol dehydrogenase are also included in the pentol dehydrogenase as long as the enzymes have the activities described above.

The reaction catalyzed by pentose reductase and pentol dehydrogenase isomerizes aldopentose to ketopentose, similarly to the reaction by pentose isomerase.

Among enzymes that catalyze isomerization of aldopentose and ketopentose, pentose isomerase of pentose may be preferably used. Xylose isomerase is more preferably used.

The gene for the xylose isomerase is not limited, and may be in the form of, for example, genomic DNA or cDNA. The gene may be derived from any of organisms including animals, plants, fungi (yeasts, molds, and the like), and bacteria. Information on such a gene can be easily known by searching a database published on a web site of, for example, NCBI. A base sequence of the xylose isomerase gene in *Escherichia coli* which may be preferably used is described in, for example, GenBank Accession No. NC_007779 REGION: 3909650 . . . 3910972.

The activity of xylose isomerase can be confirmed by performing enzyme reaction in the presence of xylose, and then measuring, by HPLC or the like, xylulose produced by isomerization. The activity of xylose isomerase can be measured by, for example, the method disclosed in JP 2008-79564 A.

Examples of organisms that may be used as the donor of the xylose isomerase include microorganisms belonging to the family Enterobacteriaceae such as the genera *Enterobacter, Escherichia, Klebsiella, Erwinia*, and *Salmonella*; actinomycetes such as the genera *Actinoplanes, Arthrobacter*, and *Streptomyces*; and the genera *Bacillus, Paenibacillus, Lactobacillus, Staphylococcus, Thermoanaerobacter, Thermus, Xanthomonas, Rhizobium, Pseudomonas, Clostridium*, and *Bacteroides*. Microorganisms belonging to the genus *Escherichia* are preferred. *Escherichia coli* is more preferred.

A gene for an enzyme having an activity to catalyze phosphorylation of ketopentose may be used. Examples of the enzyme having an activity to catalyze phosphorylation of ketopentose include xylulokinase (EC 2.7.1.17) and ribulokinase (EC 2.7.1.16). Xylulokinase may be preferably used.

The gene for the xylulokinase used is not limited, and may be in the form of, for example, genomic DNA or cDNA. The gene may be derived from any of organisms including animals, plants, fungi (yeasts, molds, and the like), and bacteria. Information on such a gene can be easily known by searching a database published on a web site of, for example, NCBI. A base sequence of the xylulokinase gene in *Escherichia coli* which may be preferably used is described in, for example, GenBank Accession No. NC_007779 REGION: 3911044 . . . 3912498.

The activity of xylulokinase can be confirmed by performing enzyme reaction in the presence of xylulose, and then measuring, by HPLC or the like, xylulose-5-phosphate produced by phosphorylation, or measuring an increase in NADPH or the like using an auxiliary enzyme reaction. For example, the measurement can be carried out by the method disclosed in Feldmann S D, Sahm H, Sprenger G A. Cloning and expression of the genes for xylose isomerase and xylulokinase from *Klebsiella pneumoniae* 1033 in *Escherichia coli* K12. Mol Gen Genet. 1992 August; 234 (2): 201-10.

Examples of organisms that may be used as the donor of the xylulokinase include microorganisms belonging to the family Enterobacteriaceae such as the genera *Enterobacter, Escherichia, Klebsiella, Erwinia*, and *Salmonella*; lactic acid bacteria such as the genera *Bacteroides* and *Lactobacillus*; actinomycetes such as the genera *Actinoplanes, Arthrobacter*, and *Streptomyces*; and the genera *Bacillus, Paenibacillus, Staphylococcus, Thermoanaerobacter, Xanthomonas, Rhizobium, Pseudomonas*, and *Clostridium*. Microorganisms belonging to the genus *Escherichia* are preferred. *Escherichia coli* is more preferred.

A gene for an enzyme having an activity of transketolase and/or transaldolase may be used. Transketolase is defined as an enzyme which catalyzes a reaction to convert xylulose-5-phosphate and erythrose-4-phosphate to fructose-6-phosphate and glyceraldehyde-3-phosphate, and the reverse reaction thereof, and/or catalyzes a reaction to convert ribose-5-phosphate and xylulose-5-phosphate to sedoheptulose-7-phosphate and glyceraldehyde-3-phosphate, and the reverse reaction thereof. The transketolase is not limited as long as it has the catalytic activity described above. For example, EC 2.2.1.1 corresponds the transketolase.

The transketolase gene and/or transaldolase gene used is/are not limited, and may be in the form of, for example, genomic DNA or cDNA. Each gene may be derived from any of organisms including animals, plants, fungi (yeasts, molds, and the like), and bacteria. Information on such genes can be easily known by searching a database published on a web site of, for example, NCBI. A base sequence of the transketolase gene in *Escherichia coli* that may be preferably used is described in, for example, GenBank Accession No. NC_007779 REGION: complement (3078300 . . . 3080291). A base sequence of the transaldolase gene in *Escherichia coli* which may be preferably used is described in, for example, GenBank Accession No. NC_007779 REGION: 8238 . . . 9191.

The activity of transketolase can be confirmed by performing enzyme reaction in the presence of xylulose-5-phosphate and erythrose-4-phosphate, and measuring, by HPLC or the like, glyceraldehyde-3-phosphate produced, or measuring a decrease in NADH or the like using an auxiliary enzyme reaction. For example, the measurement can be carried out by the method disclosed in Sprenger G A, Schorken U, Sprenger G, Sahm H. Transketolase A of *Escherichia coli* K12. Purification and properties of the enzyme from recombinant strains. Eur J Biochem. 1995 Jun. 1; 230 (2): 525-32.

Transaldolase is defined as an enzyme that catalyzes a reaction to convert sedoheptulose-7-phosphate and glyceraldehyde-3-phosphate to erythrose-4-phosphate and fructose-6-phosphate, and the reverse reaction thereof. The transaldolase is not limited as long as it has the catalytic activity described above. For example, EC2.2.1.2 corresponds the transaldolase.

The activity of transaldolase can be confirmed by performing enzyme reaction in the presence of fructose-6-phosphate and erythrose-4-phosphate, and then measuring, by HPLC or the like, glyceraldehyde-3-phosphate produced, or measuring a decrease in NADH or the like using an auxiliary enzyme reaction. For example, the measurement can be carried out by the method disclosed in GA. Sprenger, U. Schorken, G. Sprenger & H. Sahm Transaldolase B of *Escherichia coli* K-12: cloning of its gene, talB, and characterization of the enzyme from recombinant strains (J. Bacteriol., 1995, 177: 20: 5930-6).

Examples of organisms that may be used as the donor of the transaldolase and/or transketolase include microorganisms belonging to the family Enterobacteriaceae such as the genera *Enterobacter, Escherichia, Klebsiella, Erwinia*, and *Salmonella*; actinomycetes such as the genera *Actinoplanes, Arthrobacter*, and *Streptomyces*; and the genera *Bacillus, Paenibacillus, Lactobacillus, Staphylococcus, Thermoanaerobacter, Thermus, Xanthomonas, Rhizobium, Pseudomonas, Clostridium*, and *Bacteroides*. Microorganisms belonging to the genus *Escherichia* are preferred. *Escherichia coli* is more preferred.

As long as the bacterium belonging to the genus *Zymobacter* has a capacity to metabolize pentose, it may have at least any one of the genes described above introduced thereto. Preferably, exogenous genes encoding (1) xylose isomerase, (2) xylulokinase, and (3) at least one of transaldolase and transketolase, are introduced. More preferably, exogenous genes encoding (1) xylose isomerase, (2) xylulokinase, and (3) both transaldolase and transketolase, are introduced.

A microorganism other than those described above may also be used as a donor when the microorganism has a capacity to decompose xylose, or when the microorganism lacks a capacity to decompose xylose due to, for example, abnormality in a promoter site or ribosome binding site, but has DNA encoding a xylose isomerase, xylulokinase, transaldolase, and/or transketolase gene(s).

A combination of genes derived from a plurality of donors may be introduced. Such genes may be incorporated into the genomic DNA of the bacterium belonging to the genus *Zymobacter* to be used as the host, or may be present in a vector(s).

The method of introducing the gene(s) is not limited. For example, as the method of introducing the gene(s) present in the vector(s), the method disclosed in JP '421 and US '476 may be used. That is, each gene is inserted into the multicloning site of a commercially available plasmid cloning vector for *E. coli* (e.g., pUC118), and *E. coli* is then transformed with the resulting plasmid, followed by allowing the growth of the transformant producing the product of each gene. From the transformant grown, the plasmid is recovered, and the region in which each gene is introduced is cleaved out, followed by inserting the resulting fragment into the multicloning site of a wide host-range vector plasmid (e.g., pMFY31 (Agric. Biol. Chem., Vol. 49(9), 2719-2724, 1985)). By transforming a bacterium belonging to the genus *Zymobacter* with the resulting recombinant plasmid vector, a transformant belonging to the genus *Zymobacter* having a capacity to metabolize pentose can be prepared. As the wide host-range vector plasmid, a commercially available product may also be used. Methods of transformation per se are well known. For example, as described in JP '421 and JP '476, competent cells may be prepared by culturing in a medium such as T medium supplemented with magnesium ions (2.0 wt % glucose; 1.0 wt % Bacto-yeast extract; 1.0 wt % potassium dihydrogen phosphate; 0.2 wt % ammonium sulfate; 0.05 wt % magnesium sulfate heptahydrate, pH6.0). Thereafter, transformation can be carried out by a conventional method such as electroporation. A transformant having a capacity to metabolize xylose can be obtained by culturing, in a medium containing xylose as the only carbon source, the bacteria subjected to the transformation treatment.

When each gene to be introduced is incorporated into the genomic DNA, a method disclosed in, for example, Kirill A. Datsenko and Barry L. Wanner. One-step inactivation of chromosomal genes in *Escherichia coli* K-12 using PCR products. Proc Natl Acad Sci USA. Jun. 6, 2000; 97(12): 6640-6645. may be used.

Even when the fermentation feedstock contains pentose, the fermentation feedstock may contain hexose in addition to the pentose.

Pentose has five carbons constituting the sugar, and is also called five-carbon sugar. Pentose can be divided into aldopentose, which has an aldehyde group at the 1-position, and ketopentose, which has a ketone group at the 2-position. Examples of aldopentose include xylose, arabinose, ribose, and lyxose, and examples of ketopentose include ribulose and xylulose. The pentose may be any pentose as long as it can be metabolized by a microorganism, and, in view of the abundance in nature, availability and the like, xylose and arabinose are preferred, and xylose is more preferred.

Hexose has six carbons constituting the sugar, and is also called six-carbon sugar. Hexose can be divided into aldose, which has an aldehyde group at the 1-position, and ketose, which has a ketone group at the 2-position. Examples of aldose include glucose, mannose, galactose, allose, gulose, and talose, and examples of ketose include fructose, psicose, and sorbose. The hexose may be any hexose as long as it can be metabolized by a microorganism, and, in view of the abundance in nature, availability and the like, glucose, mannose, and galactose are preferred, and glucose is more preferred.

The fermentation feedstock containing pentose and hexose is not limited, and it is preferably a sugar liquid derived from a cellulose-containing biomass that is known to contain both hexose and pentose. Examples of the cellulose-containing biomass include herbaceous biomasses such as bagasse, switchgrass, corn stover, rice straw, and wheat straw; and woody biomasses such as trees and waste building materials. Cellulose-containing biomasses contain cellulose and/or hemicellulose, which are polysaccharides produced by dehydration condensation of sugars. By hydrolyzing such polysaccharides, sugar liquids that may be used as fermentation feedstocks can be produced. The method per se of preparing a sugar liquid derived from a cellulose-containing biomass is well known, and may be any method. Examples of disclosed methods of producing such a sugar include a method in which a sugar liquid is produced by acid hydrolysis of a biomass using concentrated sulfuric acid (Japanese Translated PCT Patent Application Laid-open No. 11-506934, JP 2005-229821 A), and a method in which a biomass is subjected to hydrolysis treatment using dilute sulfuric acid and then enzymatically treated with cellulase and/or the like to produce a sugar liquid (A. Aden et al., "Lignocellulosic Biomass to Ethanol Process Design and Economics Utilizing Co-Current Dilute Acid Prehydrolysis and Enzymatic Hydrolysis for Corn Stover" NREL Technical Report (2002)). Further, examples of disclosed methods in which acids are not used include a method in which a biomass is hydrolyzed using subcritical water at about 250 to 500° C. to produce a sugar liquid (JP 2003-212888 A), a method in which a biomass is subjected to subcritical water treatment and then enzymatically treated to produce a sugar liquid (JP 2001-95597 A), and a method in which a biomass is subjected to hydrolysis treatment with pressurized hot water at 240° C. to 280° C. and then enzymatically treated to produce a sugar liquid (JP 3041380 B). These treatments may be followed by purification of the obtained sugar liquid. An example of the method is disclosed in WO 2010/067785.

The weight ratio between the pentose and hexose contained in the mixed sugar is not limited, and preferably 1:9 to 9:1 as represented by the ratio of (pentose):(hexose) in terms of the weight ratio between pentose and hexose in the mixed sugar. Such a sugar ratio is expected when the mixed sugar is a sugar liquid derived from a cellulose-containing biomass.

As long as the ranges of the total sugar concentration and the ratio between pentose and hexose described above are satisfied, the concentration of hexose contained in the fermentation feedstock is not limited. By use of the method of producing 2,3-BDO, a favorable yield can be obtained even with a mixed sugar liquid containing hexose at a concentration of not less than 5 g/L.

Even when the fermentation feedstock contains pentose, the fermentation feedstock may contain, as described above, in addition to the sugars, one or more of metabolizable carbon sources, metabolizable nitrogen sources, inorganic salts, and, if necessary, amino acids and organic micronutrients such as vitamins which favorably act on the fermentation by the 2,3-butanediol fermentation microorganism, as appropriate. The fermentation feedstock may also contain an antifoaming agent for the purpose of efficient fermentation.

Even when the fermentation feedstock contains pentose, specific examples of the metabolizable nitrogen sources include, as described above, ammonia gas, aqueous ammonia, ammonium salts, urea, nitrates, and amino acids; and organic nitrogen sources which can be supplementarily used such as oil cakes, soybean hydrolysates, casein digests, corn steep liquor, yeasts or yeast extracts, meat extracts, peptides including peptone, and fermentation microorganism cells and hydrolysates thereof. Examples of inorganic salts which may be added as appropriate include phosphoric acid salts, magnesium salts, calcium salts, iron salts, manganese salts, and zinc salts. For production of 2,3-butanediol by fermentation of pentose, the fermentation feedstock preferably contains, among these components, one or more of corn steep liquor; ammonium salts such as ammonium sulfate and ammonium hydrogen phosphate; phosphoric acid salts such as potassium dihydrogen phosphate, potassium hydrogen phosphate, and ammonium hydrogen phosphate; calcium salts such as calcium chloride; iron salts such as ferrous sulfate; manganese salts such as manganese sulfate; zinc salts such as zinc sulfate; magnesium salts such as magnesium sulfate; and EDTA and salts thereof such as disodium EDTA.

Even when the fermentation feedstock contains pentose, nicotinic acid may be added to the medium as appropriate depending on the growth of the microorganism, as described above. An antifoaming agent may also be added as appropriate.

Even when the fermentation feedstock contains pentose as a metabolizable carbon source, and a microorganism belonging to the genus *Zymobacter* having a capacity to metabolize pentose is cultured, the culture temperature, the pH during the culturing, the mode of culturing of the microorganism, the aeration conditions, and the conditions for supplying oxygen into the medium, including the preferred conditions therefor, are the same as those described above.

The culture liquid obtained by the 2,3-butanediol fermentation step contains not only 2,3-butanediol, but also impurities derived from the fermentation feedstock, and ethanol as a by-product of the fermentation. Therefore, 2,3-butanediol contained in the culture liquid needs to be purified in a later process.

Purification Step

The step of purifying 2,3-butanediol from the 2,3-butanediol culture liquid is not limited, and may be carried out by a known method. Our method preferably comprises a process of distillation of the 2,3-butanediol culture liquid.

In the distillation of the 2,3-butanediol culture liquid, 2,3-butanediol is recovered from the vapor side. The method of distillation is not limited, and may be any of simple distillation, precision distillation, atmospheric distillation, and distillation under reduced pressure which are commonly applied. The method may be carried out using an apparatus selected from, for example, a thin film distillation apparatus, tray-type distillation apparatus, and packed distillation apparatus. Either a batch method or a continuous method may be applied. Distillation under reduced pressure is especially preferred since, in this method, the boiling point can be lowered to suppress generation of impurities. More specifically, the method is preferably carried out at a heating temperature of 60° C. to 150° C. When the heating temperature is less than 60° C., the pressure needs to be largely decreased so that maintenance of the apparatus is very difficult at an industrial level. When the heating temperature is more than 150° C., decomposition of a small amount of sugars and the like remaining in the 2,3-butanediol solution occurs, leading to production of colored substances as by-products, which is not preferred. Thus, the degree of reduction of the pressure is preferably controlled such that distillation of 2,3-butanediol occurs within the heating temperature range described above.

Although the 2,3-butanediol culture liquid may be subjected as it is to the distillation process, the 2,3-butanediol culture liquid is preferably subjected to a desalting process and/or a concentration process before the distillation process.

Specific examples of the desalting process include an ion-exchange process. The ion-exchange process is a method of removing ionic components in the 2,3-butanediol culture liquid using an ion exchanger. Examples of ion exchangers that may be used include ion-exchange resins, ion-exchange membranes, ion-exchange fibers, ion-exchange papers, gel ion exchangers, liquid ion exchangers, zeolite, carbonaceous ion exchangers, and montmorillonite. A process using an ion-exchange resin is preferably employed.

Ion-exchange resins can be divided into strong anion-exchange resins, weak anion-exchange resins, strong cation-exchange resins, weak cation-exchange resins, chelate-exchange resins, and the like depending on their functional groups. A strong anion-exchange resin is selected from, for example, "Amberlite" IRA410J, IRA411, and IRA910CT, manufactured by Organo Corporation; and "DIAION" SA10A, SA12A, SA11A, NSA100, SA20A, SA21A, UBK510L, UBK530, UBK550, UBK535, and UBK555, manufactured by Mitsubishi Chemical Corporation. Examples of weak anion-exchange resins include "Amberlite" IRA478RF, IRA67, IRA96SB, IRA98, and XE583, manufactured by Organo Corporation; and "DIAION" WA10, WA20, WA21J, and WA30, manufactured by Mitsubishi Chemical Corporation. Examples of strong cation-exchange resins include "Amberlite" IR120B, IR124, 200CT, and 252, manufactured by Organo Corporation; and "DIAION" SK104, SK1B, SK110, SK112, PK208, PK212, PK216, PK218, PK220, and PK228, manufactured by Mitsubishi Chemical Corporation. A weak cation-exchange resins may be selected from, for example, "Amberlite" FPC3500 and IRC76, manufactured by Organo Corporation; and "DIAION" WK10, WK11, WK100, and WK40L, manufactured by Mitsubishi Chemical Corporation.

An anion-exchange resin(s) and a cation-exchange resin(s) are preferably used in combination as the ion-exchange resin. A strong anionic resin(s) and a strong cationic resin(s) are more preferably used since these can remove various ions. The anion-exchange resin is preferably regenerated with a dilute aqueous solution of an alkali such as sodium hydroxide, and used as the OH type. The cation-exchange resin is preferably regenerated with a dilute aqueous solution of an acid such as hydrochloric acid, and used as the H type. The method of desalting using the ion-exchange resins may be either a batch method or a column method, and is not limited as long as efficient desalting is possible. In the production process, a column method is preferably employed since the method allows repeated use. The flow rate is usually controlled based on SV (space velocity), and SV is preferably 2 to 50. SV is more preferably 2 to 10 in view of achieving higher purity. Resins are commercially available in the forms of gel types such as a porous type, high porous type, and MR type, and the ion-exchange resins may be in any of these forms. Ion-exchange resins having optimum forms may be selected depending on the quality of the solution.

Specific examples of the desalting process also include nanofiltration membrane treatment. For example, in the nanofiltration membrane treatment of the 2,3-butanediol culture liquid, as disclosed in JP 2010-150248 A, filtration of the 2,3-butanediol culture liquid through a nanofiltration membrane allows efficient separation of 2,3-butanediol into the permeate side, and inorganic salts, sugars, and colored components into the feed side.

Examples of the material of the nanofiltration membrane include polymer materials such as piperazine polyamide, polyamide, cellulose acetate, polyvinyl alcohol, polyimide, and polyester; and inorganic materials such as ceramics. A nanofiltration membrane is generally used as a spiral-wound membrane element, or as a flat membrane or a hollow fiber membrane. The nanofiltration membrane is preferably a spiral-wound membrane element.

Specific examples of the nanofiltration membrane element preferably used include "GEsepa," which is a cellulose acetate nanofiltration membrane manufactured by GE Osmonics; NF99 and NF99HF, which are nanofiltration membranes having a functional layer composed of a polyamide, manufactured by Alfa-Laval; NF-45, NF-90, NF-200, and NF-400, which are nanofiltration membranes having a functional layer composed of a cross-linked piperazine polyamide, manufactured by Filmtec Corporation; and SU-210, SU-220, SU-600, and SU-610, which are nanofiltration membrane elements manufactured by Toray Industries, Inc., containing UTC60 manufactured by the same manufacturer. Among these, the nanofiltration membrane element is more preferably NF99 or NF99HF, which are nanofiltration membranes having a functional layer composed of a polyamide, manufactured by Alfa-Laval; NF-45, NF-90, NF-200, or NF-400, which are nanofiltration membranes having a functional layer composed of a cross-linked piperazine polyamide, manufactured by Filmtec Corporation; or SU-210, SU-220, SU-600, or SU-610, which are nanofiltration membrane modules manufactured by Toray Industries, Inc., containing UTC60 manufactured by the same manufacturer. The nanofiltration membrane element is still more preferably SU-210, SU-220, SU-600, or SU-610, which are nanofiltration membrane elements manufactured by Toray Industries, Inc., containing UTC60 manufactured by the same manufacturer, whose major component is a cross-linked piperazine polyamide.

Filtration through a nanofiltration membrane may be carried out under pressure, and the filtration pressure is preferably 0.1 MPa to 8 MPa. When the filtration pressure is less than 0.1 MPa, the membrane permeation rate may be low, while when the filtration pressure is more than 8 MPa, the membrane may be damaged. When the membrane is used at a filtration pressure of 0.5 MPa to 7 MPa, the membrane permeation flux is high so that the 2,3-butanediol fermentation liquid can be efficiently allowed to permeate, and the possibility of damaging the membrane is small, which is more preferred. The membrane is especially preferably used at a filtration pressure of 1 MPa to 6 MPa.

The concentration of 2,3-butanediol in the 2,3-butanediol solution that is to be filtered through the nanofiltration membrane is not limited. When the concentration of 2,3-butanediol in the 2,3-butanediol solution is high, the concentration of 2,3-butanediol contained in the permeate is also high so that the energy required for concentrating 2,3-butanediol can be saved, and the cost can therefore be reduced, which is preferred.

In the desalting process, either the ion-exchange treatment or the nanofiltration membrane treatment may be carried out, or both of these may be employed in combination. It is preferred to carry out at least the ion-exchange treatment. When the nanofiltration membrane treatment and the ion-exchange treatment are employed in combination, the order of these treatments is not limited. Preferably, the 2,3-butanediol culture liquid is subjected to the nanofiltration membrane treatment, and then the 2,3-butanediol culture liquid containing reduced inorganic salts obtained from the permeate side is subjected to the ion-exchange treatment. By this, inorganic salts and organic acids that partially pass through the nanofiltration membrane can be removed with the ion-exchange resin so that the removal rate of inorganic salts can be increased.

The method of concentrating the 2,3-butanediol culture liquid may be a general known method, and examples of the method include methods using a reverse osmosis membrane, and methods by concentration under heat using an evaporator. A method using a reverse osmosis membrane is preferably applied.

In the method using a reverse osmosis membrane, a 2,3-butanediol solution is filtered through a reverse osmosis membrane to allow water to permeate into the permeate side, while 2,3-butanediol is retained and concentrated in the feed side of the membrane. Examples of reverse osmosis membranes preferably used include composite membranes having a cellulose acetate polymer as a functional layer (hereinafter also referred to as cellulose acetate reverse osmosis membranes) and composite membranes having a polyamide functional layer (hereinafter also referred to as polyamide reverse osmosis membranes). Examples of the cellulose acetate polymer include polymers prepared with organic acid esters of cellulose such as cellulose acetate, cellulose diacetate, cellulose triacetate, cellulose propionate, and cellulose butyrate, which may be used individually, or as a mixture or mixed ester of two or more of these. Examples of the polyamide include linear polymers and cross-linked polymers constituted by aliphatic and/or aromatic diamine monomers. Examples of the form of the membrane that may be used as appropriate include a flat membrane, spiral-wound membrane, and hollow fiber membrane.

Specific examples of the reverse osmosis membrane include polyamide reverse osmosis membrane modules manufactured by Toray Industries, Inc. such as low-pressure type modules SU-710, SU-720, SU-720F, SU-710L, SU-720L, SU-720LF, SU-720R, SU-710P, and SU-720P, as well as high-pressure type modules SU-810, SU-820, SU-820L, and SU-820FA; cellulose acetate reverse osmosis membranes manufactured by the same manufacturer, SC-L100R, SC-L200R, SC-1100, SC-1200, SC-2100, SC-2200, SC-3100, SC-3200, SC-8100, and SC-8200; NTR-759HR, NTR-729HF, NTR-70SWC, ES10-D, ES20-D, ES20-U, ES15-D, ES15-U, and LF10-D, manufactured by Nitto Denko Corporation; RO98pHt, RO99, HR98PP, and CE4040C-30D, manufactured by Alfa-Laval; "GE Sepa" manufactured by GE; and BW30-4040, TW30-4040, XLE-4040, LP-4040, LE-4040, SW30-4040, and SW30HRLE-4040, manufactured by FilmTec Corporation.

The concentration through a reverse osmosis membrane is carried out under pressure. The filtration pressure is preferably 1 MPa to 8 MPa since, when the filtration pressure is less than 1 MPa, the membrane permeation rate may be low, while when the filtration pressure is more than 8 MPa, the membrane may be damaged. When the filtration pressure is 1 MPa to 7 MPa, the membrane permeation flux is high so that the 2,3-butanediol solution can be efficiently concentrated. The filtration pressure is most preferably 2 MPa to 6 MPa in view of reducing the possibility of damaging the membrane. In a 2,3-butanediol solution at a low concentration, a method using a reverse osmosis membrane is preferred in view of the cost.

Prior to the above process, a process of separating bacterial cells contained in the 2,3-butanediol culture liquid is preferably included. Examples of methods which can be used for the process of separating bacterial cells include centrifugation and filtration separation. One of, or the combination of, these methods may be employed.

The 2,3-butanediol produced by our method has high purity. Examples of methods of measuring impurities contained in the 2,3-butanediol include combinations of purity measurement by gas chromatography (GC), purity measurement by UV detection using high performance liquid chromatography (HPLC), and/or the like. Since these are based on evaluation of the ratio of the area of 2,3-butanediol in the total area of detected peaks, a higher ratio means a higher purity of 2,3-butanediol.

EXAMPLES

Our methods are described below concretely by way of Examples. However, this disclosure is not limited to these Examples.

Reference Example 1 Measurement of kLa

A dissolved-oxygen electrode (manufactured by ABLE Corporation) was inserted into a culture apparatus (manufactured by ABLE Corporation; jar capacity, 1.5 L) to measure the dissolved-oxygen level under various aeration/stirring conditions, and kLa was determined by the dynamic method using nitrogen gas. First, in the culture vessel, 1 L of water was placed, and nitrogen gas was sufficiently blown into the water while the water temperature was controlled at 30° C. and the water was stirred at a constant rate. When the electrode value became minimum, zero calibration of the dissolved-oxygen electrode was carried out. Thereafter, the aeration gas was switched from nitrogen gas to air or nitrogen gas at a predetermined aeration rate, and changes in the dissolved-oxygen level with time thereafter were measured to determine kLa. Table 1 shows kLa obtained for various aeration/stirring conditions.

TABLE 1

| Aeration rate (vvm) | Stirring rate (rpm) | kLa (h$^{-1}$) |
|---|---|---|
| 0.1 (Nitrogen gas) | 400 | 0 |
| 0.025 | 400 | 9 |
| 0.2 | 400 | 17 |
| 0.6 | 400 | 28 |
| 0.6 | 500 | 57 |

Examples 1 to 6: kLa 2,3-Butanediol Fermentation

The *Zymobacter* palmae (*Z. palmae*) ATCC51623 strain was subjected to static culture in a test tube containing 5 mL of T medium (20 g/L Glucose, 10 g/L Yeast extract, 10 g/L KH$_2$PO$_4$, 2 g/L (NH$_4$)$_2$SO$_4$, 0.5 g/L MgSO$_4$.7H$_2$O, pH 6.0) at 30° C. for 24 hours, to perform pre-preculture. The whole pre-preculture liquid was then added to an Erlenmeyer flask containing 50 mL of T medium, and static culture was carried out at 30° C. for 16 hours, to perform preculture. The preculture liquid was added to 1 L of the 2,3-butanediol fermentation medium having the composition shown in Table 2, and culturing was performed at a temperature of 30° C. at each kLa described in Table 1 while the pH was maintained at 5.5 by neutralization with potassium hydroxide. Collection of the culture liquid was carried out using an autosampler (manufactured by ABLE Corporation) at 2-hour intervals after the beginning of the culturing for up to 40 hours. The glucose concentration and the 2,3-butanediol concentration in the culture liquid collected were measured.

TABLE 2

| | |
|---|---|
| Glucose | 40 g |
| Corn steep liquor (solid content, 50%) | 30 g |
| (NH$_4$)$_2$SO$_4$ | 5.8 g |
| KH$_2$PO$_4$ | 1.75 g |
| K$_2$HPO$_4$ | 9.2 g |
| (NH$_4$)$_2$HPO$_4$ | 2.9 g |
| CaCl$_2$•2H$_2$O | 8.8 mg |
| FeSO$_4$•7H$_2$O | 44 mg |
| MnSO$_4$•5H$_2$O | 1.28 mg |
| ZnSO$_4$•7H$_2$O | 0.9 mg |
| MgSO$_4$•7H$_2$O | 219 mg |
| EDTA•2Na | 44 mg |

Unit (1/Liter)

The following are conditions for measuring each concentration by high performance liquid chromatography (HPLC, manufactured by Shimadzu Corporation). The 2,3-butanediol concentration and the glucose concentration after the fermentation, and the fermentation yield, were determined by the following measurement methods.

Measurement of 2,3-Butanediol Concentration
  Column: Shodex Sugar SH1011 (manufactured by Showa Denko K. K.)
  Column temperature: 65° C.
  Mobile phase: 0.05 M aqueous sulfuric acid solution, 0.6 mL/min.
  Detection: RI Measurement of Glucose Concentration
  Column: Asahipak NH2P50 4E (manufactured by Showa Denko K. K.)
  Column temperature: 30° C.
  Mobile phase: water:acetonitrile=1:3, 0.6 mL/min.
  Detection: RI Fermentation Yield
  Based on the 2,3-butanediol concentration and the glucose concentration measured by the above HPLC analysis, the fermentation yield was calculated using the following equation.

Fermentation yield (%)=100×{(2,3-butanediol concentration in culture liquid)−(2,3-butanediol concentration in medium)}/{(glucose concentration in medium)−(glucose concentration in culture liquid)}

The concentrations of 2,3-butanediol and glucose in the culture liquid and the fermentation yield at the time point when the glucose concentration in the culture liquid became closest to 0 are shown in Table 3. The 2,3-butanediol culture liquid obtained was recovered, and centrifuged at 4° C. at 8000 rpm for 15 minutes. The supernatant was then filtered through a microfiltration membrane (manufactured by Toray Industries, Inc.) to remove the bacterial cells. This process was carried out twice, and a total of 2 L of 2,3-butanediol culture liquid was obtained as a result.

Ion-Exchange Purification of 2,3-Butanediol Culture Liquid

The culture liquid obtained by the fermentation test described above was subjected to removal of residual ions by ion-exchange treatment. A strong anion-exchange resin IRA120J (manufactured by Organo Corporation) and a strong cation-exchange resin IR410 (manufactured by Organo Corporation) regenerated with 1 N sodium hydroxide or 1 N hydrochloric acid into the OH type or H type, respectively, were used. The amount of resin was calculated such that the total amount of inorganic salts and organic acids was the same as the exchange capacity of the ion-exchange resin. Columns were filled with the ion-exchange resins, and the culture liquid was passed through the anion-exchange resin and then through the cation-exchange resin at a flow rate SV of 5.

Distillation Purification of 2,3-Butanediol

The 2,3-butanediol solution after the ion-exchange treatment was subjected to removal of water with a film evaporator MF-10 (manufactured by Tokyo Rikakikai). At this time, water was allowed to evaporate at a degree of reduction of pressure of 30 hPa and a heating temperature of 60° C. The concentrated 2,3-butanediol solution was distilled under reduced pressure (5 mmHg) to obtain purified 2,3-butanediol. The GC purity and the distillation yield of the 2,3-butanediol after the distillation were determined by the following measurement methods.

GC Purity

The 2,3-butanediol after the distillation was analyzed by gas chromatography (GC; manufactured by Shimadzu Corporation), and the GC purity was calculated according to the following equation based on the ratio of the peak area of 2,3-butanediol in the total detected peak area.

GC purity (%)=100×(2,3-butanediol peak area)/(total detected peak area)

The analysis conditions for the gas chromatography were as follows.

Column: RT-BDEXM (0.25 mm×30 m, manufactured by Restek)

Column temperature: 75° C.

Vaporizing chamber, detector temperature: 230° C.

Carrier gas: He

Linear velocity: 35 cm/sec.

Detection: flame ionization detector (FID)

Distillation Yield

The distillation yield was calculated according to the following equation based on the amount of 2,3-butanediol fed before the distillation calculated from the 2,3-butanediol concentration measured by HPLC analysis and the amount of liquid fed, and the recovery of 2,3-butanediol calculated from the amount of distillate after the distillation and the above-described GC purity.

Distillation yield (%)=100×{(amount of distillate after distillation)×(GC purity)}/{(2,3-butanediol concentration before distillation)×(amount of liquid fed before distillation)}

Total 2,3-Butanediol Yield

The total 2,3-butanediol yield was calculated according to the following equation based on the fermentation yield calculated from the results of the fermentation step, and the distillation yield calculated from the results of the purification step. The results on the total 2,3-butanediol yield are shown in Table 3.

Total 2,3-butanediol yield (g/g sugar)=(fermentation yield)/100×(distillation yield)/100

TABLE 3

| | | Example 1 | Example 2 | Example 3 | Example 4 | Example 5 | Example 6 |
|---|---|---|---|---|---|---|---|
| | kLa (h$^{-1}$) | 0 | 3 | 9 | 17 | 28 | 57 |
| Before culturing | Glucose concentration (g/L) | 42.0 | 42.1 | 42.0 | 40.8 | 39.5 | 41.1 |
| | 2,3-BDO concentration (g/L) | 0.0 | 0.0 | 0.0 | 0.0 | 0.0 | 0.0 |
| After culturing | Glucose concentration (g/L) | 26.1 | 11.6 | 2.1 | 0.5 | 0.2 | 3.4 |
| | 2,3-BDO concentration (g/L) | 1.1 | 7.8 | 16.0 | 18.9 | 18.2 | 17.5 |
| | Fermentation yield (%) | 6.8 | 25.5 | 40.0 | 46.8 | 46.4 | 46.5 |
| After distillation | Distillation yield (%) | 78.6 | 79.3 | 82.4 | 82.6 | 83.2 | 82.7 |
| | GC purity (%) | >99.9 | >99.9 | >99.9 | >99.9 | >99.9 | >99.9 |
| Total 2,3-BDO yield (g/g sugar) | | 0.053448 | 0.202215 | 0.3296 | 0.386568 | 0.386048 | 0.384555 |

Examples 7 to 11: pH

The *Z. palmae* ATCC51623 strain was cultured by the pre-preculture method and the preculture method described in Examples 1 to 6. The preculture liquid was added to 1 L of the 2,3-butanediol fermentation medium having the composition shown in Table 2, and culturing was carried out at an aeration rate of 0.2 vvm, stirring rate of 400 rpm, and temperature of 30° C. while the pH was maintained at one of 4.5, 4.8, 5.2, 5.5, 6.1, and 6.5 by neutralization with potassium hydroxide. Collection of the culture liquid was carried out using an autosampler (manufactured by ABLE Corporation) at 2-hour intervals after the beginning of the culturing for up to 40 hours. The glucose concentration and the 2,3-butanediol concentration in the culture liquid collected were measured according to the methods described in Examples 1 to 6. The concentrations of 2,3-butanediol and glucose in the culture liquid and the fermentation yield at the time point when the glucose concentration in the culture liquid became closest to 0 are shown in Table 4. The 2,3-butanediol culture liquid after the fermentation test was recovered, and centrifuged at 4° C. at 8000 rpm for 15 minutes. The supernatant was then filtered through a microfiltration membrane (manufactured by Toray Industries, Inc.) to remove the bacterial cells. This process was carried out twice, and a total of 2 L of 2,3-butanediol culture liquid was obtained as a result. The culture liquid obtained was subjected to desalting and distillation treatment by the methods described in Examples 1 to 6 to obtain purified 2,3-butanediol. The GC purity and the distillation yield of the 2,3-butanediol after the distillation were determined by the methods described in Examples 1 to 6. The results are shown in Table 4.

liquid after the fermentation test was recovered, and centrifuged at 4° C. at 8000 rpm for 15 minutes. The supernatant was then filtered through a microfiltration membrane (manu-

TABLE 4

|  |  | Example 7 | Example 8 | Example 9 | Example 10 | Example 11 |
|---|---|---|---|---|---|---|
| Before culturing | pH | 4.5 | 4.8 | 5.2 | 6.1 | 6.5 |
|  | Glucose concentration (g/L) | 41.5 | 41.6 | 42.0 | 40.4 | 38.8 |
|  | 2,3-BDO concentration (g/L) | 0.0 | 0.0 | 0.0 | 0.0 | 0.0 |
| After culturing |  | 4.5 | 4.8 | 5.2 | 6.1 | 6.5 |
|  | Glucose concentration (g/L) | 11.5 | 0.0 | 2.3 | 1.6 | 2.6 |
|  | 2,3-BDO concentration (g/L) | 6.5 | 12.4 | 18.1 | 18.5 | 13.8 |
|  | Fermentation yield (%) | 21.5 | 29.8 | 45.7 | 47.7 | 38.0 |
| After distillation | Distillation yield (%) | 79.1 | 81.5 | 82.9 | 82.6 | 83.2 |
|  | GC purity (%) | >99.9 | >99.9 | >99.9 | >99.9 | >99.9 |
| Total 2,3-BDO yield (g/g sugar) |  | 0.170065 | 0.24287 | 0.378853 | 0.394002 | 0.31616 |

Examples 12 to 16: Sugar Concentration

The *Z. palmae* ATCC51623 strain was cultured by the pre-preculture method and the preculture method described in Examples 1 to 6. The preculture liquid was added to 1 L of the 2,3-butanediol fermentation medium having the same composition as shown in Table 2 except that the glucose concentration was adjusted to one of 12, 20, 100, 180, and 250 g/L. Culturing was then carried out at an aeration rate of 0.2 vvm, stirring rate of 400 rpm, and temperature of 30° C. while the pH was maintained at 5.5 by neutralization with potassium hydroxide. Collection of the culture liquid was carried out using an autosampler (manufactured by ABLE Corporation) at 2- to 8-hour intervals after the beginning of the culturing. The glucose concentration and the 2,3-butanediol concentration in the culture liquid collected were measured according to the methods described in Examples 1 to 6. The concentrations of 2,3-butanediol and glucose in the culture liquid and the fermentation yield at the time point when the glucose concentration in the culture liquid became closest to 0 are shown in Table 5. The 2,3-butanediol culture liquid after the fermentation test was recovered, and centrifuged at 4° C. at 8000 rpm for 15 minutes. The supernatant was then filtered through a microfiltration membrane (manufactured by Toray Industries, Inc.) to remove the bacterial cells. This process was carried out twice, and a total of 2 L of 2,3-butanediol culture liquid was obtained as a result. The culture liquid obtained was subjected to desalting and distillation treatment by the methods described in Examples 1 to 6 to obtain purified 2,3-butanediol. The GC purity and the distillation yield of the 2,3-butanediol after the distillation were determined by the methods described in Examples 1 to 6. The results are shown in Table 5.

TABLE 5

|  |  | Example 12 | Example 13 | Example 14 | Example 15 | Example 16 |
|---|---|---|---|---|---|---|
| Before culturing | Glucose concentration (g/L) | 12.5 | 20.4 | 100.8 | 187.7 | 253.9 |
|  | 2,3-BDO concentration (g/L) | 0.0 | 0.0 | 0.0 | 0.0 | 0.0 |
| After culturing | Glucose concentration (g/L) | 0.0 | 0.4 | 3.1 | 0.3 | 5.6 |
|  | 2,3-BDO concentration (g/L) | 5.3 | 8.8 | 44.2 | 82.6 | 115.5 |
|  | Fermentation yield (%) | 42.4 | 44.2 | 45.2 | 44.1 | 46.5 |
| After distillation | Distillation yield (%) | 78.8 | 79.5 | 84.6 | 84.3 | 86.4 |
|  | GC purity (%) | >99.9 | >99.9 | >99.9 | >99.9 | >99.9 |
| Total 2,3-BDO yield (g/g sugar) |  | 0.334112 | 0.35139 | 0.382392 | 0.371763 | 0.40176 |

Examples 17 to 31

Expression of four kinds of enzyme genes in cells of the transformant described in JP '421 and US '476 was confirmed. This transformant has been deposited with International Patent Organism Depositary, National Institute of Advanced Industrial Science and Technology, under accession No. FERM BP-10048 as of Jun. 30, 2004, under the Budapest Treaty.

Examples 17 to 21: kLa

2,3-Butanediol Fermentation

As a microorganism belonging to the genus *Zymobacter* given a capacity to metabolize xylose, *Zymobacter palmae* [pMFY31-xt] disclosed in JP '421 and US '476 was used. *Zymobacter palmae* [pMFY31-xt] is a known transformant prepared by transformation of *Zymobacter palmae* with a recombinant wide host-range vector plasmid to which exogenous genes encoding xylose isomerase, xylulokinase, transaldolase, and transketolase are introduced. As described above, *Zymobacter palmae* [pMFY31-xt] has been deposited under accession No. FERM BP-10048 under the Budapest Treaty, and is available. *Z. palmae* [pMFY31-xt] was subjected to static culture in a test tube containing 5 mL of TX medium (40 g/L Xylose, 10 g/L Yeast extract, 10 g/L $KH_2PO_4$, 2 g/L $(NH_4)_2SO_4$, 0.5 g/L $MgSO_4 \cdot 7H_2O$, pH 6.0) supplemented with 100 μg/mL ampicillin, at 30° C. for 24 hours. The whole culture liquid was then added to an Erlenmeyer flask containing 50 mL of TX medium, and static culture was carried out at 30° C. for 24 hours. The whole culture liquid was then added to 1 L of the 2,3-butanediol fermentation medium having the composition shown in Table 6, and culturing was performed at a temperature of 30° C. under the aeration/stirring conditions described in Table 1 while the pH was maintained at 5.5 by neutralization with potassium hydroxide. The culture liquid was collected as appropriate during the culturing, and the xylose concentration and the 2,3-butanediol concentration were measured.

TABLE 6

| | |
|---|---|
| Xylose | 40 g |
| Corn steep liquor | 30 g |
| $(NH_4)_2SO_4$ | 5.8 g |
| $KH_2PO_4$ | 1.75 g |
| $K_2HPO_4$ | 9.2 g |
| $(NH_4)_2HPO_4$ | 2.9 g |
| $CaCl_2 \cdot 2H_2O$ | 8.8 mg |
| $FeSO_4 \cdot 7H_2O$ | 44 mg |
| $MnSO_4 \cdot 5H_2O$ | 1.28 mg |
| $ZnSO_4 \cdot 7H_2O$ | 0.9 mg |
| $MgSO_4 \cdot 7H_2O$ | 219 mg |
| $EDTA \cdot 2Na$ | 44 mg |

Unit (1/Liter)

The following are conditions for measuring each concentration by high performance liquid chromatography (HPLC, manufactured by Shimadzu Corporation). The 2,3-butanediol concentration and the sugar concentration after the fermentation, and the fermentation yield, were determined by the following measurement methods.

Measurement of 2,3-Butanediol Concentration
  Column: Shodex Sugar SH1011 (manufactured by Showa Denko K. K.)
  Column temperature: 65° C.
  Mobile phase: 0.05 M aqueous sulfuric acid solution, 0.6 mL/min.
  Detection: RI Measurement of Sugar Concentration
  Column: Asahipak NH2P50 4E (manufactured by Showa Denko K. K.)
  Column temperature: 30° C.
  Mobile phase: water:acetonitrile=1:3, 0.6 mL/min.
  Detection: RI Fermentation Yield
Based on the 2,3-butanediol concentration and the sugar concentration measured by the above HPLC analysis, the fermentation yield was calculated using the following equation.

Fermentation yield (%)=100×{(2,3-butanediol concentration in culture liquid)−(2,3-butanediol concentration in medium)}/{(sugar concentration in medium)−(sugar concentration in culture liquid)}

The concentrations of 2,3-butanediol and xylose in the culture liquid and the fermentation yield at the time point when the xylose concentration in the culture liquid became closest to 0 are shown in Table 7. The 2,3-butanediol culture liquid obtained was recovered, and centrifuged at 4° C. at 8000 rpm for 15 minutes. The supernatant was then filtered through a microfiltration membrane (manufactured by Toray Industries, Inc.) to remove the bacterial cells. This process was carried out twice, and a total of 2 L of 2,3-butanediol culture liquid was obtained as a result.

Ion-Exchange Purification of 2,3-Butanediol Culture Liquid
The culture liquid obtained by the fermentation test described above was subjected to removal of residual ions by ion-exchange treatment. A strong anion-exchange resin IRA120J (manufactured by Organo Corporation) and a strong cation-exchange resin IR410 (manufactured by Organo Corporation) that were regenerated with 1 N sodium hydroxide or 1 N hydrochloric acid into the OH type or H type, respectively, were used. The amount of resin was calculated such that the total amount of inorganic salts and organic acids was the same as the exchange capacity of the ion-exchange resin. Columns were filled with the ion-exchange resins, and the culture liquid was passed through the anion-exchange resin and then through the cation-exchange resin at a flow rate SV of 5.

Distillation Purification of 2,3-Butanediol
The 2,3-butanediol solution after the ion-exchange treatment was subjected to removal of water with a film evaporator MF-10 (manufactured by Tokyo Rikakikai). At this time, water was allowed to evaporate at a degree of reduction of pressure of 30 hPa and a heating temperature of 60° C. The concentrated 2,3-butanediol solution was distilled under reduced pressure (5 mmHg) to obtain purified 2,3-butanediol. The GC purity and the distillation yield of the 2,3-butanediol after the distillation were determined by the following measurement methods.

GC Purity
The 2,3-butanediol after the distillation was analyzed by gas chromatography (GC; manufactured by Shimadzu Corporation), and the GC purity was calculated according to the following equation based on the ratio of the peak area of 2,3-butanediol in the total detected peak area.

GC purity (%)=100×(2,3-butanediol peak area)/(total detected peak area)

The analysis conditions for the gas chromatography were as follows.
  Column: RT-BDEXM (0.25 mm×30 m, manufactured by Restek)
  Column temperature: 75° C.
  Vaporizing chamber, detector temperature: 230° C.
  Carrier gas: He
  Linear velocity: 35 cm/sec.
  Detection: flame ionization detector (FID)

Distillation Yield

The distillation yield was calculated according to the following equation based on
the amount of 2,3-butanediol fed before the distillation calculated from the 2,3-butanediol concentration measured by HPLC analysis and the amount of liquid fed, and
the recovery of 2,3-butanediol calculated from the amount of distillate after the distillation and the above-described GC purity.

Distillation yield (%)=100×{(amount of distillate after distillation)×(GC purity)}/{(2,3-butanediol concentration before distillation)×(amount of liquid fed before distillation)}

Total 2,3-Butanediol Yield

The total 2,3-butanediol yield was calculated according to the following equation based on the fermentation yield calculated from the results of the fermentation step, and the distillation yield calculated from the results of the purification step. The results on the total 2,3-butanediol yield are shown in Table 7.

Total 2,3-butanediol yield (g/g sugar)=(fermentation yield)/100×(distillation yield)/100

Examples 22 to 25: pH

Z. palmae [pMFY31-xt] was cultured by the method described in Examples 17 to 21. The resulting culture liquid, prepared by culturing in a flask, was added to 1 L of the 2,3-butanediol fermentation medium having the composition shown in Table 6, and culturing was carried out at an aeration rate of 0.2 vvm, stirring rate of 400 rpm, and temperature of 30° C. while the pH was maintained at one of 4.5, 4.8, 6.1, and 6.5 by neutralization with potassium hydroxide. The culture liquid was collected as appropriate during the culturing, and the xylose concentration and the 2,3-butanediol concentration were measured by the methods described in Examples 17 to 21. The concentrations of 2,3-butanediol and xylose in the culture liquid and the fermentation yield at the time point when the xylose concentration in the culture liquid became closest to 0 are shown in Table 8. The 2,3-butanediol culture liquid after the fermentation test was recovered, and centrifuged at 4° C. at 8000 rpm for 15 minutes. The supernatant was then filtered through a microfiltration membrane (manufactured by Toray Industries, Inc.) to remove the bacterial cells. This process was carried out twice, and a total of 2 L of 2,3-butanediol culture liquid was obtained as a result. The culture liquid obtained was subjected to desalting and distillation treatment by the methods described in Examples 17 to 21 to obtain purified 2,3-butanediol. The GC purity and the distillation yield of the 2,3-butanediol after the distillation were determined by the methods described in Examples 17 to 21. The results are shown in Table 8.

TABLE 7

|  |  | Example 17 | Example 18 | Example 19 | Example 20 | Example 21 |
|---|---|---|---|---|---|---|
|  | kLa ($h^{-1}$) | 0 | 9 | 17 | 28 | 57 |
| Before culturing | Xylose concentration (g/L) | 41.8 | 41.7 | 41.2 | 39.9 | 41.3 |
|  | 2,3-BDO concentration (g/L) | 0.0 | 0.0 | 0.0 | 0.0 | 0.0 |
| After culturing | Xylose concentration (g/L) | 5.8 | 20.8 | 0.0 | 1.1 | 0.0 |
|  | 2,3-BDO concentration (g/L) | 6.1 | 4.6 | 10.3 | 10.3 | 11.1 |
|  | Fermentation yield (%) | 17.0 | 22.0 | 25.0 | 26.6 | 26.8 |
| After distillation | Distillation yield (%) | 80.3 | 81.9 | 82.5 | 82.4 | 82.3 |
|  | GC purity (%) | >99.9 | >99.9 | >99.9 | >99.9 | >99.9 |
| Total 2,3-BDO yield (g/g sugar) |  | 0.13651 | 0.18018 | 0.20625 | 0.219184 | 0.220564 |

TABLE 8

|  |  | Example 22 | Example 23 | Example 24 | Example 25 |
|---|---|---|---|---|---|
|  | pH | 4.5 | 4.8 | 6.1 | 6.5 |
| Before culturing | Xylose concentration (g/L) | 41.6 | 39.8 | 41.0 | 40.6 |
|  | 2,3-BDO concentration (g/L) | 0.0 | 0.0 | 0.0 | 0.0 |
| After culturing | Xylose concentration (g/L) | 13.6 | 0.8 | 0.0 | 0.3 |
|  | 2,3-BDO concentration (g/L) | 3.7 | 7.7 | 9.3 | 6.1 |
|  | Fermentation yield (%) | 13.1 | 19.7 | 22.8 | 15.2 |
| After distillation | Distillation yield (%) | 80.7 | 82.2 | 83.0 | 82.8 |
|  | GC purity (%) | >99.9 | >99.9 | >99.9 | >99.9 |
| Total 2,3-BDO yield (g/g sugar) |  | 0.105717 | 0.161934 | 0.18924 | 0.125856 |

Examples 26 to 28: Sugar Concentration

*Z. palmae* [pMFY31-xt] was cultured by the method described in Examples 17 to 21. The resulting culture liquid, prepared by culturing in a flask, was added to 1 L of the 2,3-butanediol fermentation medium having the same composition as shown in Table 6 except that the xylose concentration was adjusted to one of 5.0, 15, and 100 g/L. Culturing was then carried out at an aeration rate of 0.2 vvm, stirring rate of 400 rpm, and temperature of 30° C. while the pH was maintained at 5.5 by neutralization with potassium hydroxide. The culture liquid was collected as appropriate during the culturing, and the xylose concentration and the 2,3-butanediol concentration were measured by the methods described in Examples 17 to 21. The concentrations of 2,3-butanediol and xylose in the culture liquid and the fermentation yield at the time point when the xylose concentration in the culture liquid became closest to 0 are shown in Table 9. The 2,3-butanediol culture liquid after the fermentation test was recovered, and centrifuged at 4° C. at 8000 rpm for 15 minutes. The supernatant was then filtered through a microfiltration membrane (manufactured by Toray Industries, Inc.) to remove the bacterial cells. This process was carried out twice, and a total of 2 L of 2,3-butanediol culture liquid was obtained as a result. The culture liquid obtained was subjected to desalting and distillation treatment by the methods described in Examples 17 to 21 to obtain purified 2,3-butanediol. The GC purity and the distillation yield of the 2,3-butanediol after the distillation were determined by the methods described in Examples 17 to 21. The results are shown in Table 9.

TABLE 9

| | | Example 26 | Example 27 | Example 28 |
|---|---|---|---|---|
| Before culturing | Xylose concentration (g/L) | 5.3 | 12.8 | 95.8 |
| | 2,3-BDO concentration (g/L) | 0.0 | 0.0 | 0.0 |
| After culturing | Xylose concentration (g/L) | 0.0 | 0.0 | 18.6 |
| | 2,3-BDO concentration (g/L) | 1.5 | 3.5 | 17.1 |
| | Fermentation yield (%) | 28.2 | 27.4 | 22.2 |
| After distillation | Distillation yield (%) | 78.9 | 79.2 | 85.9 |
| | GC purity (%) | >99.9 | >99.9 | >99.9 |
| Total 2,3-BDO yield (g/g sugar) | | 0.222498 | 0.217008 | 0.190698 |

Examples 29 to 31: Pentose Ratio

*Z. palmae* [pMFY31-xt] was cultured by the method described in Examples 17 to 21. The resulting culture liquid, prepared by culturing in a flask, was added to 1 L of the 2,3-butanediol fermentation medium having the same composition as shown in Table 6 except that the xylose and glucose concentrations (g/L) were adjusted to one of (40: 20), (20:40), and (2.5:40), respectively. Culturing was then carried out at an aeration rate of 0.2 vvm, stirring rate of 400 rpm, and temperature of 30° C. while the pH was maintained at 5.5 by neutralization with potassium hydroxide. The culture liquid was collected as appropriate during the culturing, and the sugar concentration and the 2,3-butanediol concentration were measured by the methods described in Examples 17 to 21. The 2,3-butanediol concentration and the sugar concentration in the culture liquid and the fermentation yield at the time point when the sugar concentration in the culture liquid became closest to 0 are shown in Table 10. The 2,3-butanediol culture liquid after the fermentation test was recovered, and centrifuged at 4° C. at 8000 rpm for 15 minutes. The supernatant was then filtered through a microfiltration membrane (manufactured by Toray Industries, Inc.) to remove the bacterial cells. This process was carried out twice, and a total of 2 L of 2,3-butanediol culture liquid was obtained as a result. The culture liquid obtained was subjected to desalting and distillation treatment by the methods described in Examples 17 to 21 to obtain purified 2,3-butanediol. The GC purity and the distillation yield of the 2,3-butanediol after the distillation were determined by the methods described in Examples 17 to 21. The results are shown in Table 10.

TABLE 10

|  |  | Example 29 | Example 30 | Example 31 |
|---|---|---|---|---|
| Before culturing | Xylose concentration (g/L) | 2.6 | 23.9 | 40.5 |
|  | Glucose concentration (g/L) | 40.3 | 45.9 | 19.8 |
|  | 2,3-BDO concentration (g/L) | 0.0 | 0.0 | 0.0 |
| After culturing | Xylose concentration (g/L) | 0.0 | 2.0 | 4.3 |
|  | Glucose concentration (g/L) | 0.0 | 0.0 | 0.0 |
|  | 2,3-BDO concentration (g/L) | 18.7 | 21.0 | 15.3 |
|  | Fermentation yield (%) | 43.6 | 30.9 | 27.4 |
| After distillation | Distillation yield (%) | 83.2 | 84.3 | 84.1 |
|  | GC purity (%) | >99.9 | >99.9 | >99.9 |
| Total 2,3-BDO yield (g/g sugar) |  | 0.362752 | 0.260487 | 0.230434 |

Examples 32 to 35: Organic Nitrogen Source

The *Z. palmae* ATCC51623 strain was cultured by the pre-preculture method and the preculture method described in Examples 1 to 6. The preculture liquid was added to 1 L of the 2,3-butanediol fermentation medium having the same composition as shown in Table 2 except that the corn steep liquor was replaced with various organic nitrogen sources shown in Table 11. Culturing was then carried out at an aeration rate of 0.2 vvm, stirring rate of 400 rpm, and temperature of 30° C. while the pH was maintained at 5.5 by neutralization with potassium hydroxide. Collection of the culture liquid was carried out using an autosampler (manufactured by ABLE Corporation) at 2- to 4-hour intervals after the beginning of the culturing. The glucose concentration and the 2,3-butanediol concentration in the culture liquid collected were measured by the methods described in Examples 1 to 6. The concentrations of 2,3-butanediol and glucose in the culture liquid and the fermentation yield at the time point when the glucose concentration in the culture liquid became closest to 0 are shown in Table 12. The 2,3-butanediol culture liquid after the fermentation test was recovered, and centrifuged at 4° C. at 8000 rpm for 15 minutes. The supernatant was then filtered through a microfiltration membrane (manufactured by Toray Industries, Inc.) to remove the bacterial cells. This process was carried out twice, and a total of 2 L of 2,3-butanediol culture liquid was obtained as a result. The culture liquid obtained was subjected to desalting and distillation treatment by the methods described in Examples 1 to 6 to obtain purified 2,3-butanediol. The GC purity and the distillation yield of the 2,3-butanediol after the distillation were determined by the methods described in Examples 1 to 6. The results are shown in Table 12.

A good 2,3-BDO yield could be obtained with any of the organic nitrogen sources. The highest 2,3-BDO yield could be obtained in the case where corn steep liquor was used as shown in Example 4.

TABLE 11

| Organic nitrogen source | Concentration (g/L, in terms of solid content) |
|---|---|
| Soybean hydrolysate | 15 |
| Animal tissue hydrolysate | 15 |
| Casein hydrolysate | 15 |
| Yeast extract | 15 |

TABLE 12

|  |  | Example 32 | Example 33 | Example 34 | Example 35 |
|---|---|---|---|---|---|
| Organic nitrogen source |  | Soybean hydrolysate | Animal tissue hydrolysate | Casein hydrolysate | Yeast extract |
| Before culturing | Glucose concentration (g/L) | 39.8 | 41.1 | 40.5 | 39.7 |
|  | 2,3-BDO concentration (g/L) | 0.0 | 0.0 | 0.0 | 0.0 |
| After culturing | Glucose concentration (g/L) | 0.3 | 3.1 | 1.1 | 0.0 |
|  | 2,3-BDO concentration (g/L) | 16.3 | 11.7 | 10.8 | 12.3 |
|  | Fermentation yield (%) | 41.2 | 30.9 | 27.4 | 30.9 |
| After distillation | Distillation yield (%) | 83.1 | 81.9 | 82.3 | 79.6 |
|  | GC purity (%) | >99.9 | >99.9 | >99.9 | >99.9 |
| Total 2,3-BDO yield (g/g sugar) |  | 0.342372 | 0.253071 | 0.225502 | 0.245964 |

INDUSTRIAL APPLICABILITY 2,3-Butanediol (2,3-BDO) obtained by our method is a useful compound as an intermediate material for pharmaceuticals and cosmetics, and as a material for inks, perfumes, liquid crystals, insecticides, softening agents, explosives, plasticizers and the like.

The invention claimed is:

1. A method of producing 2,3-butanediol, comprising:
    culturing a microorganism belonging to genus *Zymobacter* in a fermentation feedstock containing a carbon source (Step A); and
    purifying 2,3-butanediol from culture liquid obtained in said step (Step B),
    wherein said Step A is culturing at a volumetric oxygen transfer coefficient (kLa) of not less than 9 $h^{-1}$.
2. The method according to claim 1, wherein said microorganism is *Zymobacter palmae*.

3. The method according to claim 1, wherein said Step A is culturing at a pH of 5 to 7.

4. The method according to claim 1, wherein said Step A is culturing in a medium whose total sugar concentration is not less than 20 g/L.

5. The method according to claim 1, wherein said carbon source contains a pentose, and said microorganism belonging to the genus *Zymobacter* has a capacity to metabolize said pentose.

6. The method according to claim 1, wherein said microorganism is a transformed microorganism belonging to the genus *Zymobacter* in which an exogenous gene(s) encoding at least one enzyme selected from the group consisting of xylose isomerase, xylulokinase, transaldolase, and transketolase is/are introduced.

7. The method according to claim 6, wherein said microorganism is a transformed microorganism belonging to the genus *Zymobacter* in which exogenous genes encoding xylose isomerase, xylulokinase, transaldolase, and transketolase are introduced.

8. The method according to claim 5, wherein said pentose contained in said fermentation feedstock in said Step A is xylose.

9. The method according to claim 5, wherein the abundance of xylose with respect to total sugar in said fermentation feedstock is 5 to 100%.

10. The method according to claim 5, wherein said fermentation feedstock contains a sugar liquid derived from a biomass.

11. The method according to claim 1, wherein said fermentation feedstock in said Step A contains corn steep liquor.

12. The method according to claim 1, wherein said Step B comprises a distillation process.

13. The method according to claim 12, comprising a desalting process before said distillation process.

14. The method according to claim 13, comprising an ion-exchange process as said desalting process.

\* \* \* \* \*